United States Patent
Tyrrell et al.

(10) Patent No.: US 6,673,627 B2
(45) Date of Patent: *Jan. 6, 2004

(54) WHOLE BLOOD COLLECTION DEVICE

(75) Inventors: Steven P. Tyrrell, Highland Park, IL (US); Barbara R. Grzeda, Schaumburg, IL (US)

(73) Assignee: BioSafe Medical Technologies, Inc., Lake Forest, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 10/131,768

(22) Filed: Apr. 24, 2002

(65) Prior Publication Data

US 2002/0182744 A1 Dec. 5, 2002

Related U.S. Application Data

(63) Continuation-in-part of application No. 09/464,757, filed on Dec. 16, 1999, now Pat. No. 6,406,919.

(51) Int. Cl.[7] .................................................. G01N 1/00
(52) U.S. Cl. .................. 436/174; 436/69; 436/169; 436/179; 436/180; 422/99; 422/102; 422/58; 600/573
(58) Field of Search ................ 436/63, 69, 174, 436/176, 177, 179, 180, 164, 169; 422/99, 102, 58, 61; 435/287.3, 288.4, 288.5; 600/573, 577, 578

(56) References Cited

U.S. PATENT DOCUMENTS

| | | | |
|---|---|---|---|
| 3,640,267 A | 2/1972 | Hurtig et al. | 600/578 |
| 4,378,333 A | 3/1983 | Laipply | 422/100 |
| 4,957,582 A | 9/1990 | Columbus | 156/332 |
| 5,163,442 A | 11/1992 | Ono | 600/573 |
| 5,200,152 A | 4/1993 | Brown | 422/102 |
| 5,310,523 A | 5/1994 | Smethers et al. | 422/57 |
| 5,316,952 A * | 5/1994 | Brimhall | 436/70 |
| 5,503,803 A | 4/1996 | Brown | 422/102 |
| 5,638,828 A | 6/1997 | Lauks et al. | 600/573 |
| 5,651,766 A | 7/1997 | Kingsley et al. | 604/6.04 |
| 5,674,457 A | 10/1997 | Williamsson et al. | 422/102 |
| 5,824,268 A | 10/1998 | Bernstein et al. | 422/56 |
| 6,036,659 A | 3/2000 | Ray et al. | 600/573 |
| 6,406,919 B1 * | 6/2002 | Tyrrell | 436/174 |

FOREIGN PATENT DOCUMENTS

| WO | WO 79/01131 | 12/1979 |
|---|---|---|
| WO | WO 99/57559 | 11/1999 |

* cited by examiner

Primary Examiner—Maureen M. Wallenhorst
(74) Attorney, Agent, or Firm—Olson & Hierl, Ltd.

(57) ABSTRACT

A system for collecting a whole blood sample includes a fill port (32), a metering chamber (72), a gasket or seal (16) and a reservoir (74). The gasket or seal (16) is positioned to a fill position, and a sample of whole blood is received in the metering chamber (72) until the metering chamber (72) is full. Then the seal (16) is moved to a closed position, thereby moving blood from the metering chamber (72) to the reservoir (74) and also sealing the reservoir (74). The seal (16), metering chamber (72) and fill port (32) together define a passageway at least a portion of which is coated with an anticoagulant. A diluting liquid contained in the reservoir (74) is mixed with the whole blood to dilute and stabilize the whole blood in the reservoir (74) for later analysis of one or more selected blood components.

31 Claims, 10 Drawing Sheets

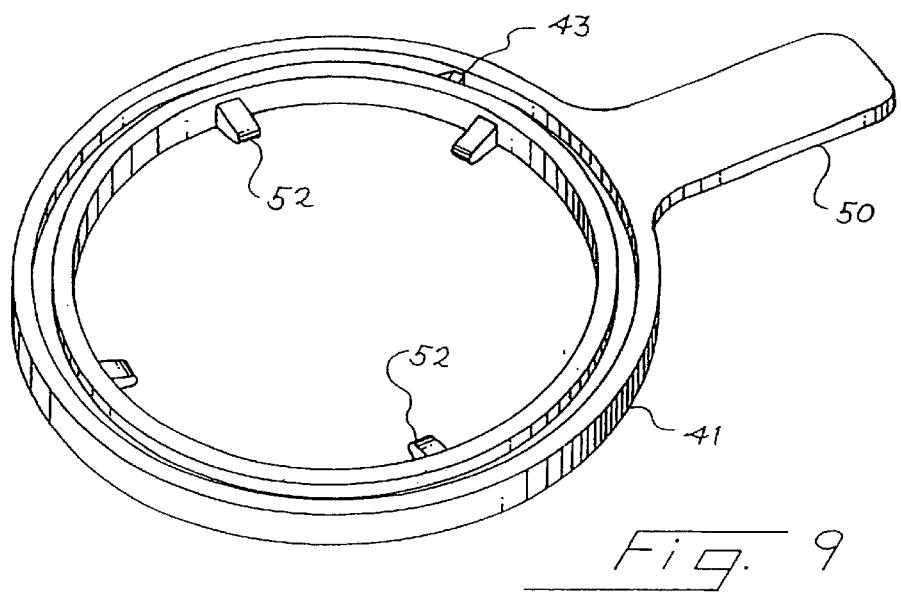
Fig. 9
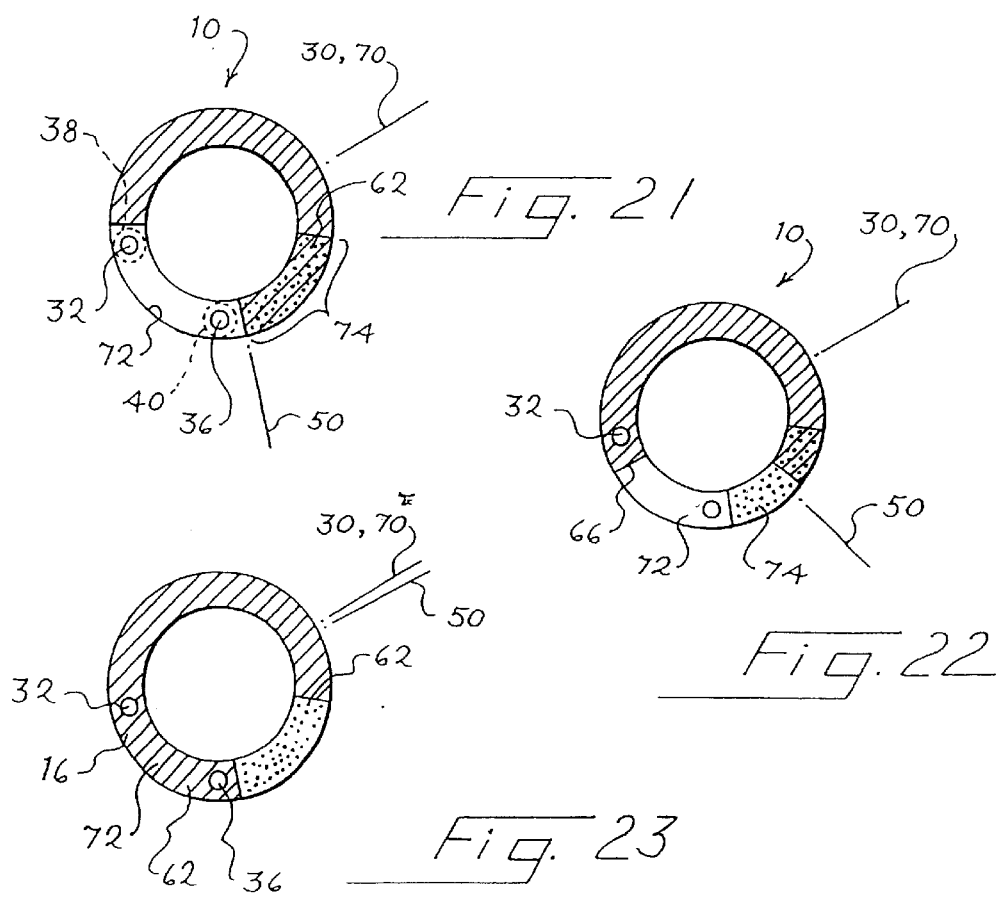
Fig. 21
Fig. 22
Fig. 23

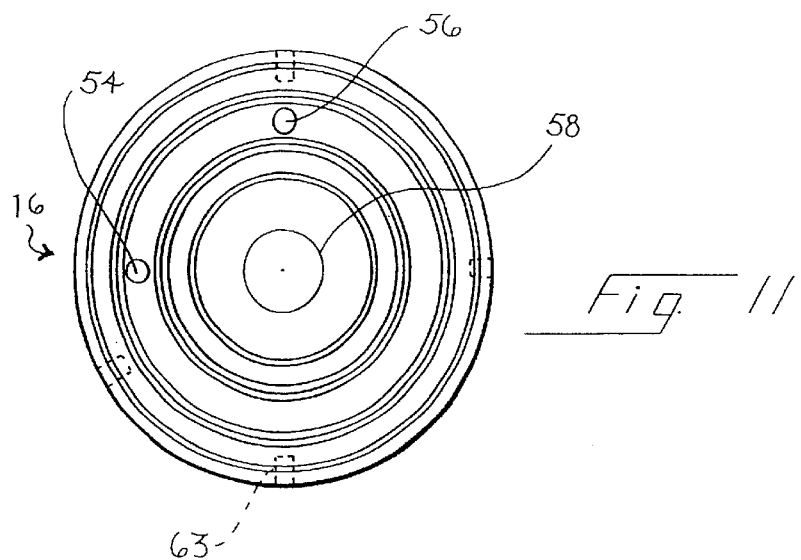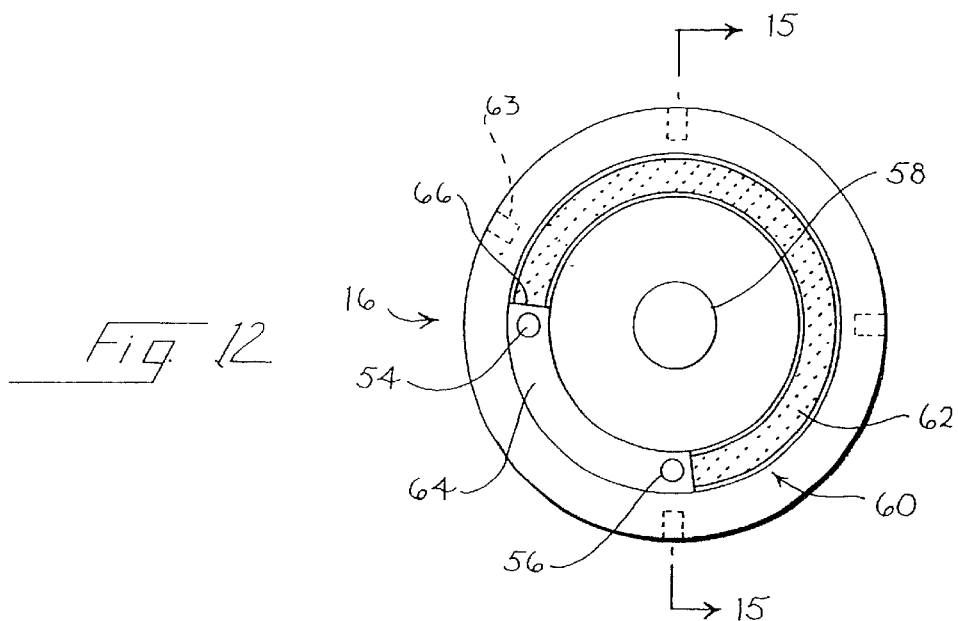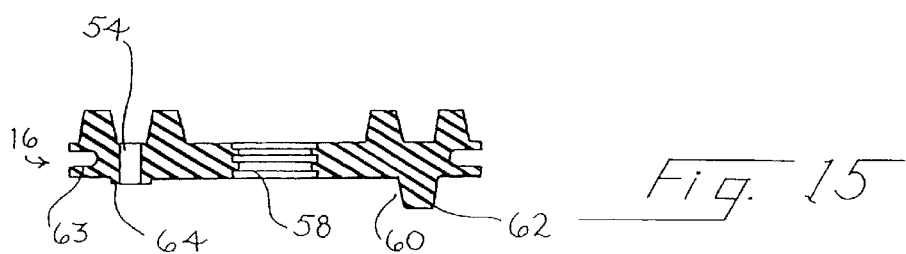

WHOLE BLOOD COLLECTION DEVICE

CROSS-REFERENCE TO RELATED APPLICATION

This application is a continuation-in-part of application U.S. Ser. No. 09/464,757, filed on Dec. 16, 1999, now U.S. Pat. No. 6,406,919 issued on Jun. 18, 2002.

TECHNICAL FIELD OF THE INVENTION

This invention relates to whole blood collection devices for use in blood sampling. More particularly, the present invention relates to a collection device and method that allows whole blood to be collected precisely and reliably at a remote site and then shipped to a central laboratory for analysis.

BACKGROUND OF THE INVENTION

In the past, it has been common practice for a physician to require an individual to come to a laboratory or office to have whole blood drawn for clinical analysis. This represents a substantial inconvenience to the individual, however, it has been considered a necessary prerequisite for obtaining a suitable blood sample for many types of blood tests. A need presently exists for an improved system that overcomes this inefficiency by allowing a patient to obtain a blood sample at home, for example, and to then ship the self-collected sample to a clinical laboratory for testing. In addition, many physicians could benefit from a reliable blood collection device that allows for minimally invasive collection of blood samples in their office during patient visits.

There is an ongoing need, therefore, for a reliable blood testing apparatus that can be used by an individual without assistance of medical personnel or in a clinical office setting, which provides a reliable, minimally invasive means of collecting blood samples for off-site clinical analysis. The present invention fulfills this need.

SUMMARY OF THE INVENTION

The blood collection device of the present invention is a compact, self-contained, handheld blood sample collection and storage device that can be conveniently used by an individual without assistance of medical personnel. The blood collection device is designed to collect a specific quantity of blood that is sufficient for selected clinical blood analyses. The device can be configured to collect enough blood for a single blood clinical analysis or for several analyses. Preferably, the device is configured to collect a sufficient quantity of blood for a single analytical test protocol. The device of the present invention is also a storage device for safely and reliably preserving the collected blood sample during shipment to a clinical laboratory for analysis.

In a preferred embodiment described below, the device is configured to collect a precisely metered volume of whole blood without the need for training, and without the need for the user to perform complex techniques. The system can dilute the whole blood and seal the diluted blood in the device when the user simply turns a lever. By diluting blood at the point of collection, blood stability is improved. Blood dilution also improves the likelihood that the analyzing laboratory will have an adequate physical sample of liquid with which to work, once the specimen reaches the laboratory for analysis. If desired, a stabilizing composition can be placed in the diluting liquid to stabilize specific blood components prior to analysis.

The present whole blood sample collection device defines a reservoir for a collected whole blood sample, a metering chamber that initially receives the whole blood sample and empties into the reservoir, and a fill port that communicates with and empties into the metering chamber. The collection device is also provided with a movable seal or gasket that can isolate the reservoir from the metering chamber. When the seal or gasket is in a fill position, the reservoir is isolated from the metering chamber and a liquid flow passageway is defined between the fill port and the metering chamber so that a whole blood sample can be received into the metering chamber via the fill port. When the seal or gasket is in an intermediate position, the metering chamber can be isolated from the fill port as well as from the reservoir. When the seal or gasket is in a closed position, the seal isolates the fill port from the metering chamber but a fluid flow passageway is defined between the reservoir and the metering chamber so that there exists fluid flow communication between the reservoir and the metering chamber, and the blood sample contained in the metering chamber can be swept into the reservoir for storage and subsequent analysis.

The whole blood sample collection device of the present invention also includes a mechanism for delivery of anticoagulant to the blood sample, inasmuch as an anticoagulant is generally required for most analyses that can be performed on blood stored for a period of time before testing. In one embodiment of the invention, the anticoagulant is supplied to the blood by passing the blood through a pad that has been impregnated with anticoagulant. The anticoagulant impregnated pad is integrally positioned within the blood receiving portion of the device so that blood must flow through the pad to enter the sample storage and dilution chamber of the device. In another embodiment, interior surfaces of portions of the device that define a blood sample passageway within the device, and that are designed to contact the blood sample are coated with an anticoagulant, so that as the blood contacts these surfaces an anticoagulant is delivered to the blood sample. The anticoagulant coated surfaces can be used in conjunction with an anticoagulant impregnated pad, or the coated surfaces themselves can act as the sole anticoagulant delivery source in the device.

A surface wetting agent such as a nonionic surfactant can also be included in the anticoagulant coating. The wetting agent can serve a dual purpose of promoting efficient flow of blood into the sample storage chamber and facilitating the deposition of a substantially uniform anticoagulant coating on the blood contact surfaces of the device during manufacture.

BRIEF DESCRIPTION OF THE DRAWINGS

In the drawings,

FIGS. 7, 8 and 9 are top, bottom, and upper perspective views, respectively, of a middle plate included in the device of FIG. 1;

FIGS. 11, 12, 13 and 14 are top, bottom, upper perspective and lower perspective views, respectively, of a gasket adapted for mounting to the middle plate of FIGS. 7 through 10;

FIG. 15 is a cross-sectional view taken along plane 15—15 of FIG. 12;

FIGS. 21, 22 and 23 are schematic views of selected elements of the device of FIG. 1 in the filling, intermediate, and closed positions, respectively.

DESCRIPTION OF PREFERRED EMBODIMENTS

Figure 1:
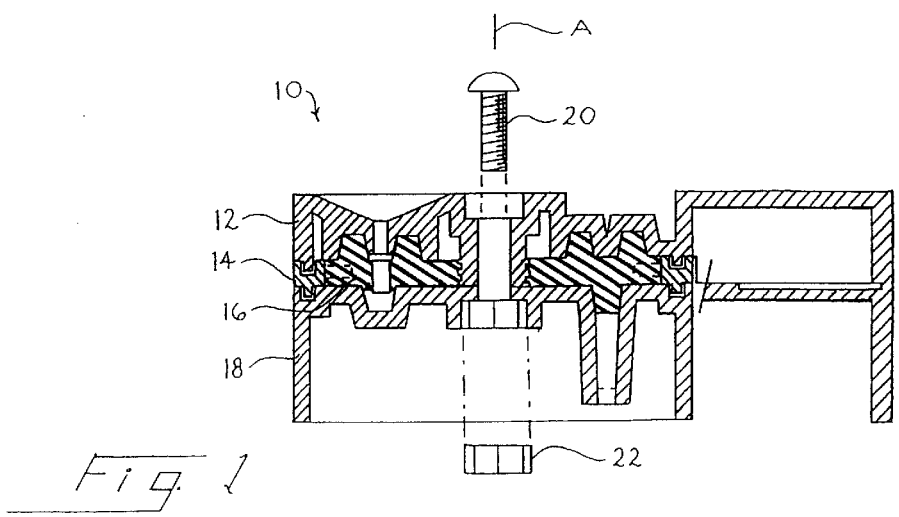
FIG. 1 is a cross-sectional view of a preferred embodiment of a blood collection device of the present invention.
Figure 2:
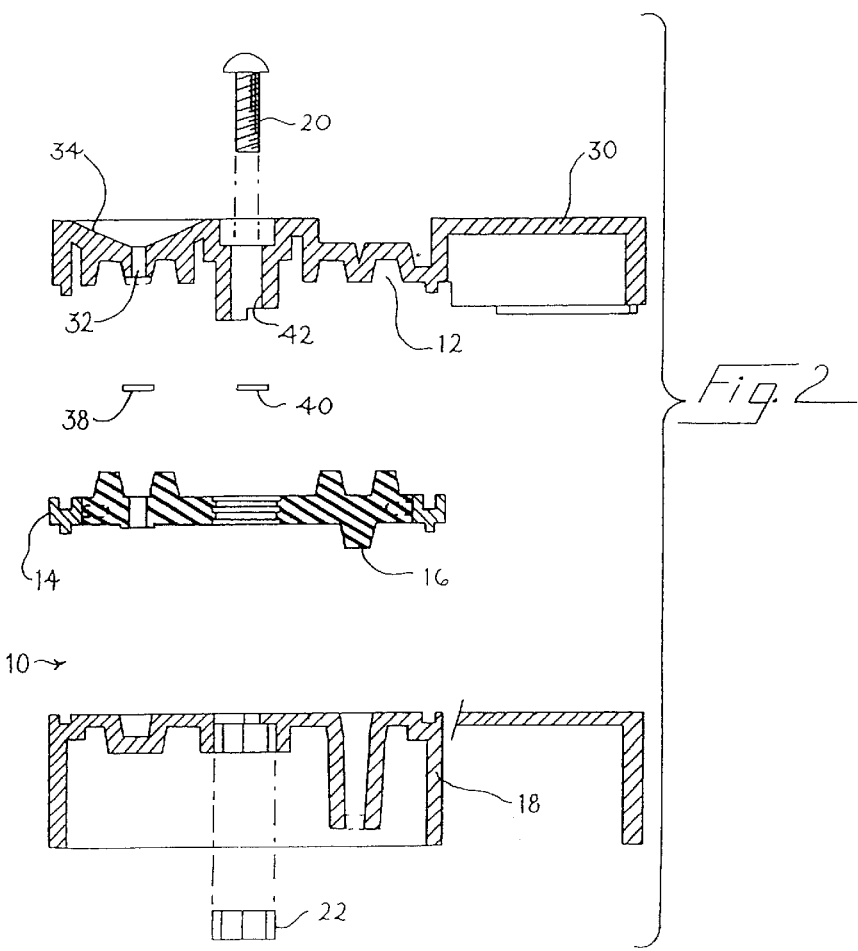
FIG. 2 is an exploded view of the device of FIG. 1.
Figure 3:
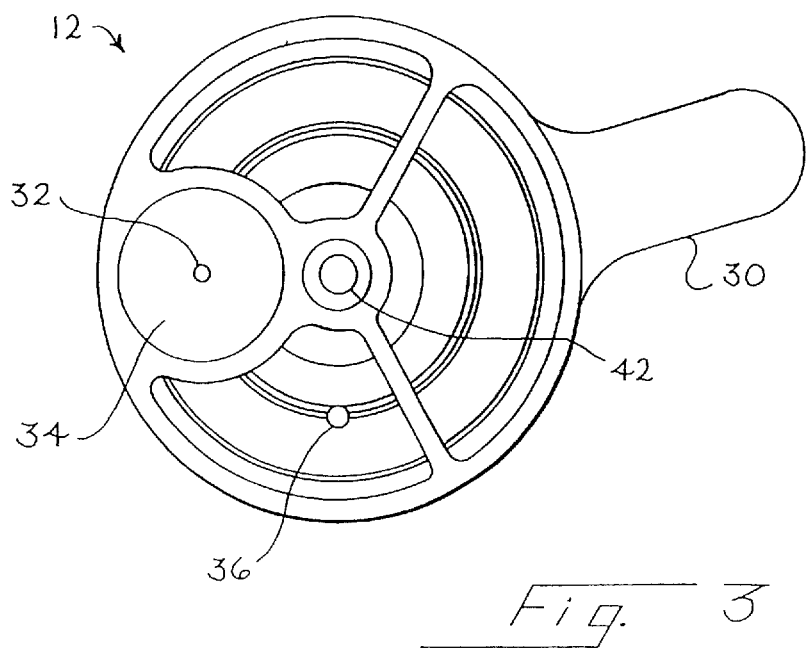
FIGS. 3, 4, 5 and 6 are top, bottom, upper perspective and lower perspective views, respectively, of an upper plate included in the device of FIG. 1.

Turning now to the drawings, FIG. 1 shows a cross-sectional view of a whole blood collection device 10 that incorporates a preferred embodiment of this invention. The device 10 is a small, disposable device that has been configured for use by an untrained individual to collect a small volume of whole blood sample for later analysis. The device 10 includes an upper plate 12 with fill port 32, a middle plate 14 that supports a gasket or seal 16, and a lower plate 18. The device 10 is held together by a screw 20 and a nut 22. The screw 20 defines an axis of rotation (A) substantially normal to the plane of plates 12 and 18. The middle plate 14 and the movable gasket or seal 16 are mounted for rotation about the axis A as described below. FIG. 2 provides an exploded cross sectional view of the elements of FIG. 1.

Figure 4:
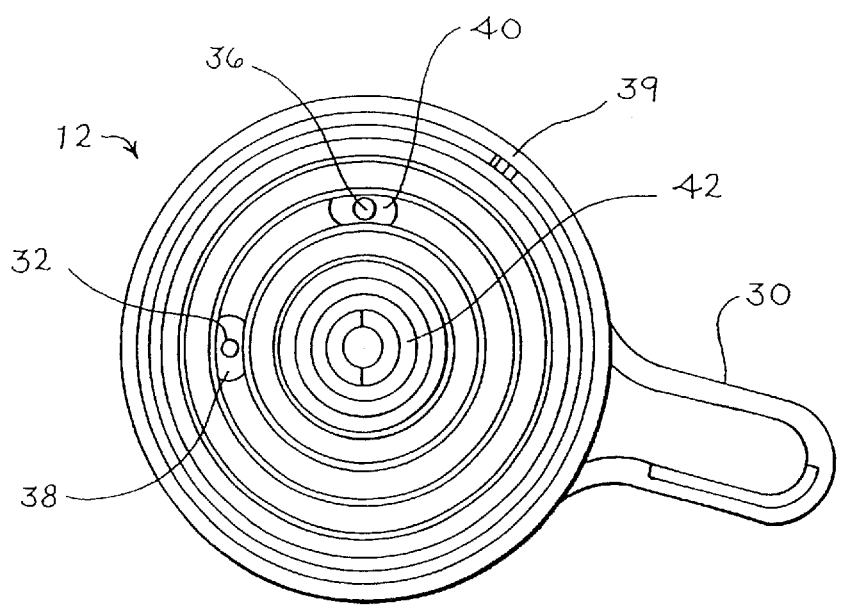
Figure 5:
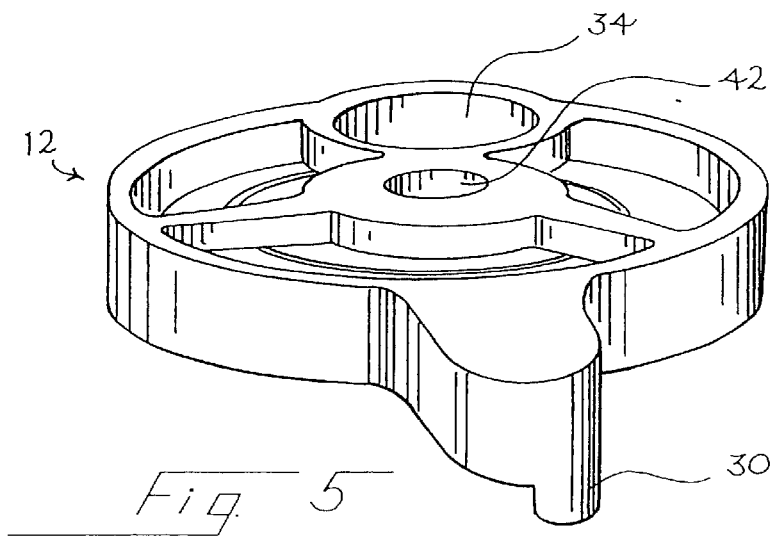
Figure 6:
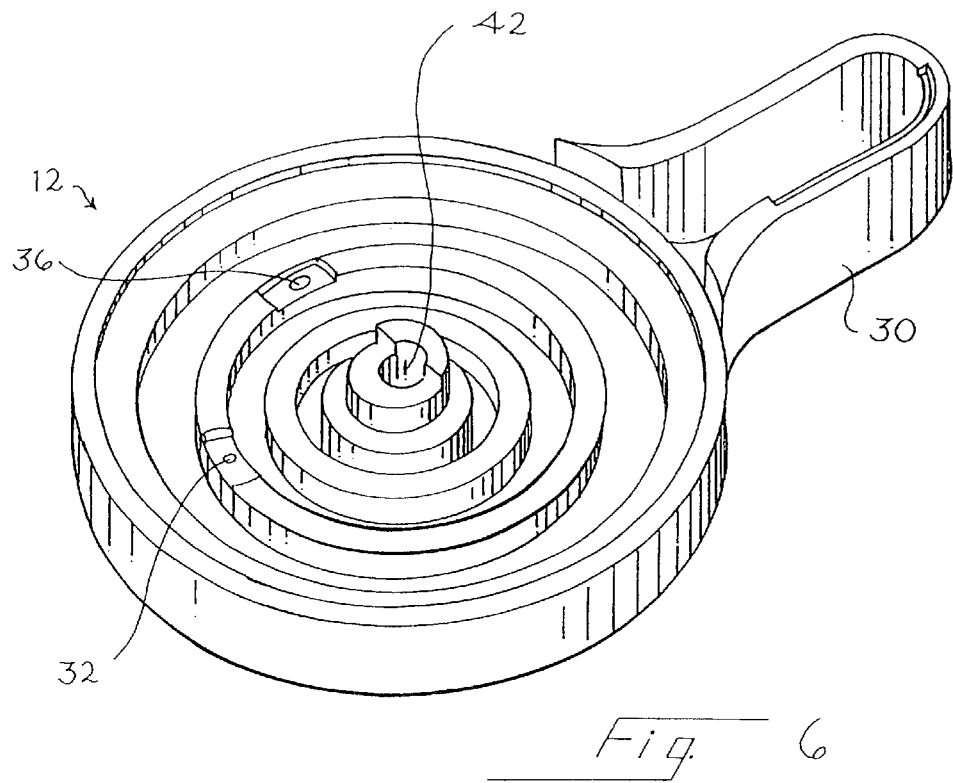

As best shown in FIGS. 2–6, the upper plate 12 includes a radially extending handle 30. In addition to fill port 32, the upper plate 12 also defines a view port 36. Both ports extend completely through the upper plate 12. A funnel 34 surrounds the fill port 32. An anticoagulant pad 38 is mounted under the fill port 32, and a view port pad 40 is mounted under the view port 36. The pad 38 is a porous sheet impregnated with an anticoagulant. Blood passing through the fill port 32 mixes with this anticoagulant as it passes through the pad 38. The upper plate 12 also defines a central opening 42 centered around the axis A, and the lower surface of the upper plate 12 includes a latching element 39 (FIG. 4).

Figure 10:
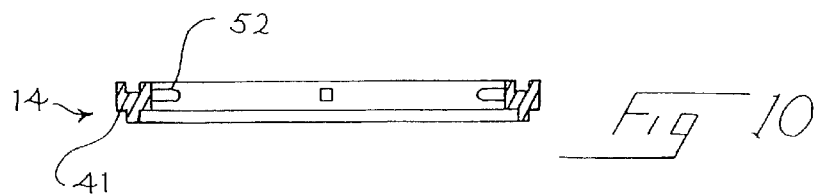
FIG. 10 is a cross-sectional view taken along plane 10—10 of FIG. 7.
Figure 13:
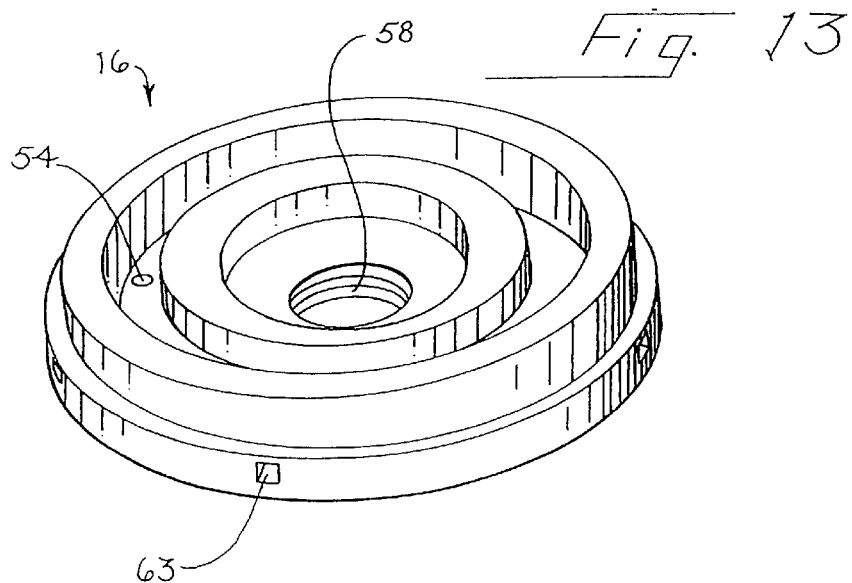
Figure 14:
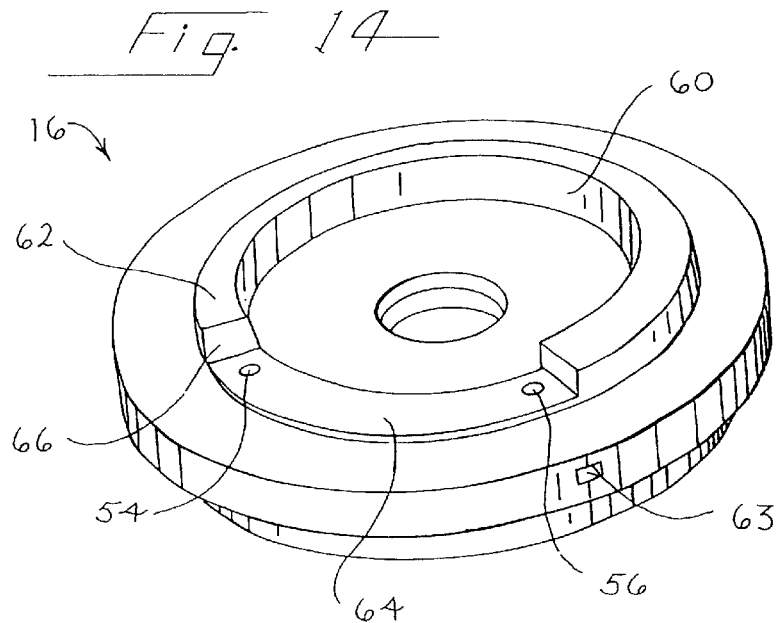
Figure 16:
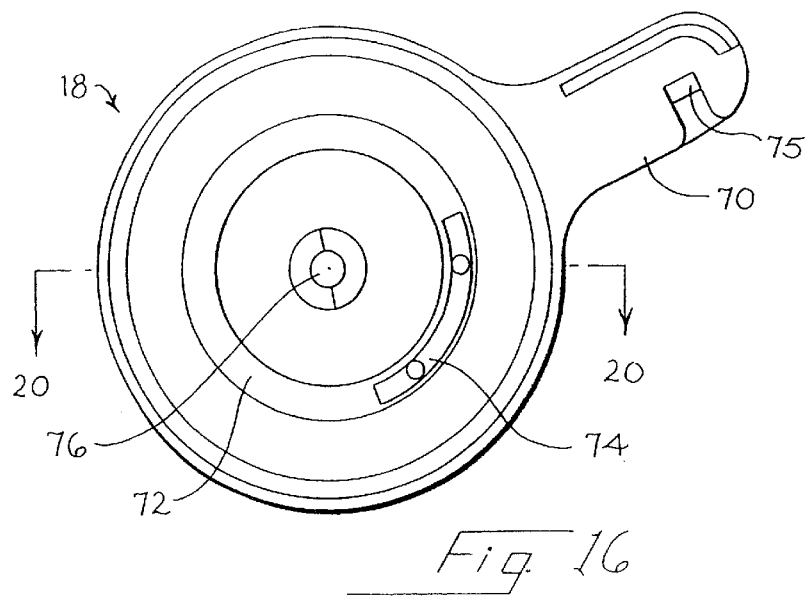
FIGS. 16, 17, 18 and 19 are top, bottom, upper perspective and lower perspective views, respectively, of a lower plate included in the device of FIG. 1.
Figure 17:
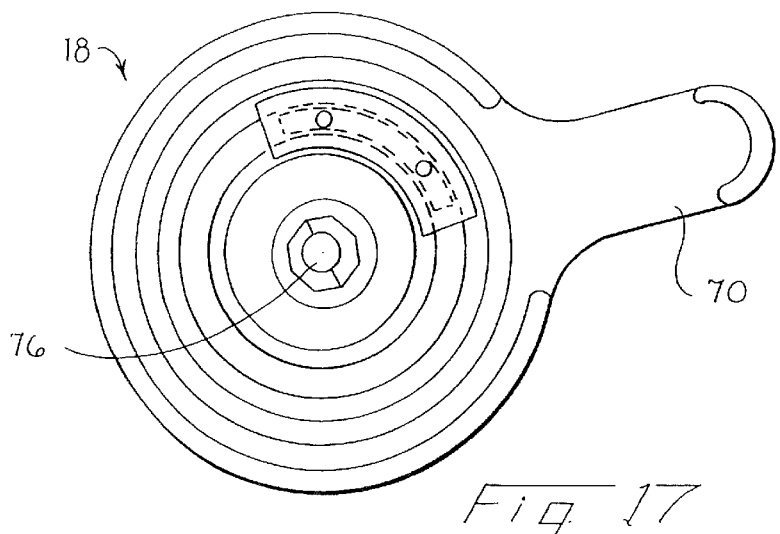

As best shown in FIGS. 7, 8, 9, and 10, the middle plate 14 includes a circular rim 41 that supports a radially extending handle 50 and inwardly extending tabs 52. The tabs 52 secure the gasket or seal 16 to the middle plate 14 and prevent relative movement therebetween (FIG. 10). A first latching element 43 (in this case in the form of a ramp) is positioned on the upper side of the rim 41. A second latching element 45 (in this case also in the form of a ramp) is formed in the lower face of the handle 50.

As best shown in FIGS. 11–14, the gasket or seal 16 defines a fill port through-hole 54 and a view port through-hole 56 that are positioned to align with the fill port 32 and the view port 36, respectively, of the upper plate 12 when the middle plate 14 and the gasket 16 are positioned in a fill position. The gasket or seal 16 also defines a central opening 58 sized to receive the screw of FIG. 1.

Figure 7:
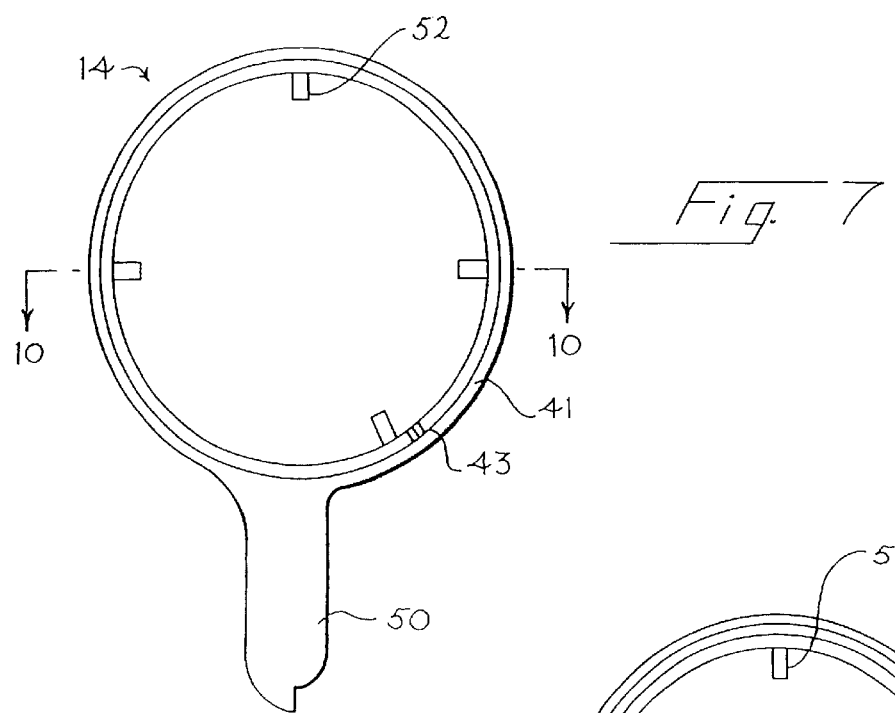
Figure 8:
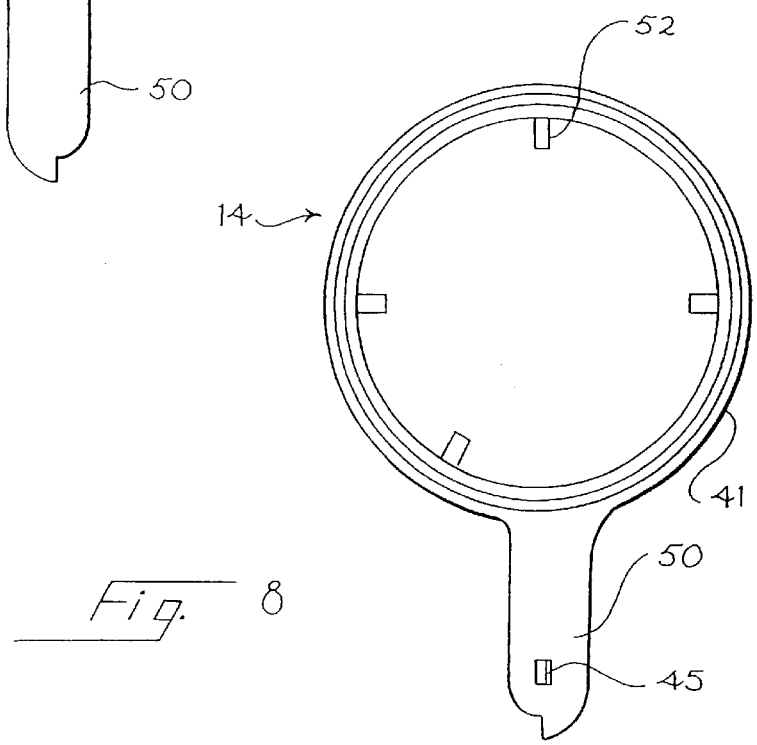

A protruding element 60 extends from the lower surface of the gasket 16. This protruding element 60 is annular in shape, and it includes two separate portions 62, 64. The first portion 62 extends over an arc of about 245 degrees, as shown in FIG. 12, and it extends substantially away from the plane of the seal or gasket 16, as shown in FIG. 15. The second portion 64 of the protruding element 60 extends over an arc of about 115 degrees (FIG. 12) and extends only a small distance beyond the lower surface of the seal or gasket 16 (FIG. 15). As shown in FIG. 12, the through-holes 54, 56 are located in the second portion 64 of the protruding element 60. A leading portion of the first portion 62 of the protruding element 60 acts as a sweeping element 66, as described in detail below. Gasket or seal 16 also defines recesses 63, which are positioned to receive the tabs 52 of the middle plate 14 (FIGS. 7–9).

Figure 20:
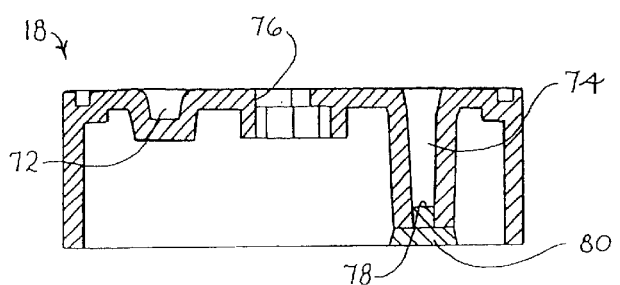
FIG. 20 is a cross-sectional view taken along plane 20—20 of FIG. 16.
Figure 18:
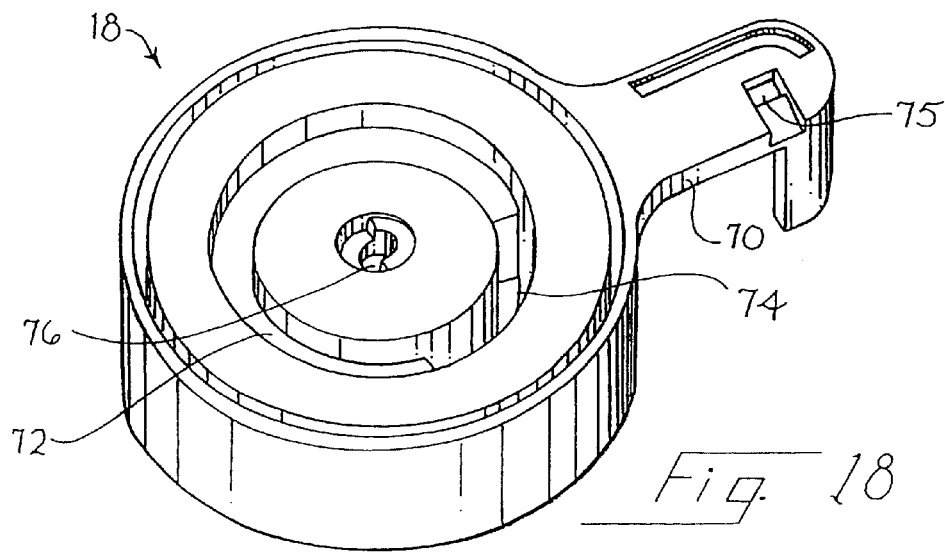
Figure 19:
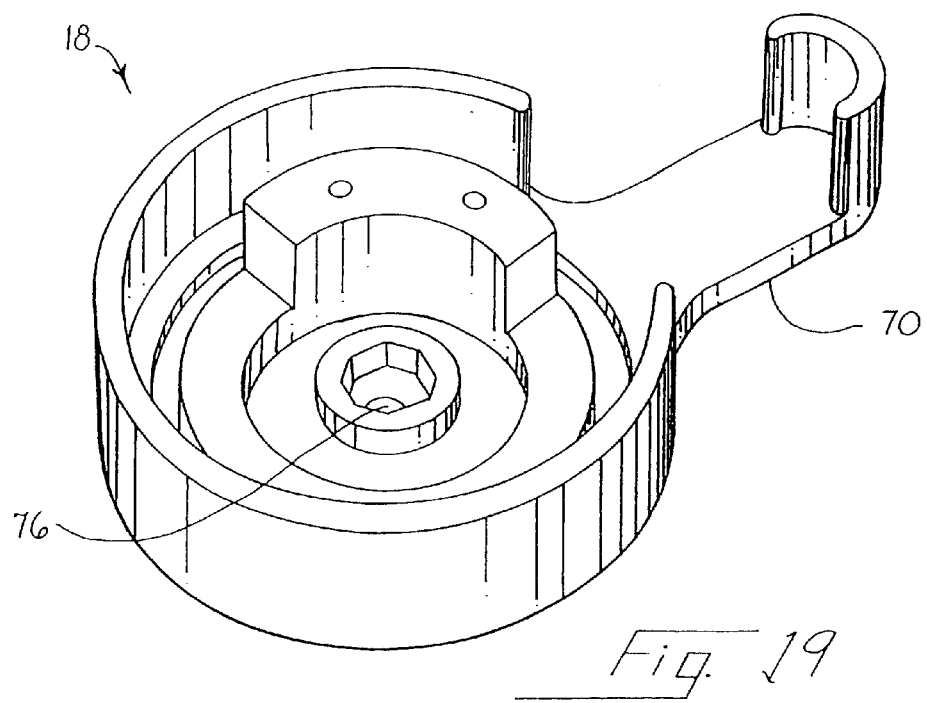

FIGS. 16–20 provide further illustration regarding the construction of the lower plate 18. Lower plate 18 defines a central opening 76 and an annular capillary channel 72 on its upper surface, concentric with the central opening 76. Plate 18 also includes a handle 70 that extends radially away from a central opening 76. As shown in FIG. 20, the capillary channel 72 has a relatively shallow depth. In this embodiment the sidewalls of the capillary channel 72 each diverge by an included angle of about 10 degrees with respect to a line drawn perpendicularly to the upper surface of the lower plate 18. The capillary channel 72 is proportioned to receive and be sealed by the first portion 62 of the protruding element 60 of the gasket 16 (FIGS. 11–14).

The capillary channel 72 together with upper plate 12 and seal or gasket 16 defines a metering chamber that empties at both ends into a reservoir 74 that is also concentric with the central opening 76. As shown in FIG. 20, the reservoir 74 is substantially deeper than the capillary channel 72, and the bottom of the reservoir 74 defines two access ports 78, each of which is sealed by a plug 80. The upper surface of the handle 70 supports a latching element 75. Depending upon the position of the seal or gasket 16, a liquid flow passageway is defined between fill port 32 in upper plate 12 and the metering chamber when the seal or gasket 16 is in fill position. When the seal or gasket 16 is in closed position, a liquid passageway is defined between the metering chamber and reservoir 74.

The latching elements 39, 75 on the upper and lower plates 12, 18, respectively, cooperate with mating latching elements 43, 45 on the middle plate 14 to form a snap latch. The snap latch holds the handle 50 inside a recess formed by the handles 30, 70 once the middle plate 14 has been moved to the closed position described below.

FIGS. 21–24 provide a schematic representation of the use of the device 10 for collecting blood sample for analysis. As shown at block 100 in the flow diagram of FIG. 24, the device 10 (FIG. 21) is provided to a user, such as an individual desiring to obtain a laboratory analysis of any suitable blood component. As selected examples, the device 10 can be used to obtain a complete blood count (CBC), and/or an analysis of blood lipids, thyroid stimulating hormone (TSH), or prostate specific antigen (PSA). Other blood components can also be analyzed, such as hematocrit, hemoglobin A1c, blood glucose, or luteinizing hormone, for example.

In its initial configuration, the collection device 10 is positioned with the seal or gasket 16 supported by middle plate 14 in the fill position shown in FIG. 21. In the fill position both the fill port 32 and the view port 36 are aligned with the corresponding openings 54 and 56 in the gasket and with the capillary channel 72 that defines part of a metering chamber. The capillary channel 72 is isolated from the reservoir 74 by the first portion 62 of the protruding element 60. In the fill position the handles 30, 70 and 50 are positioned as schematically shown in FIG. 21.

Figure 24:
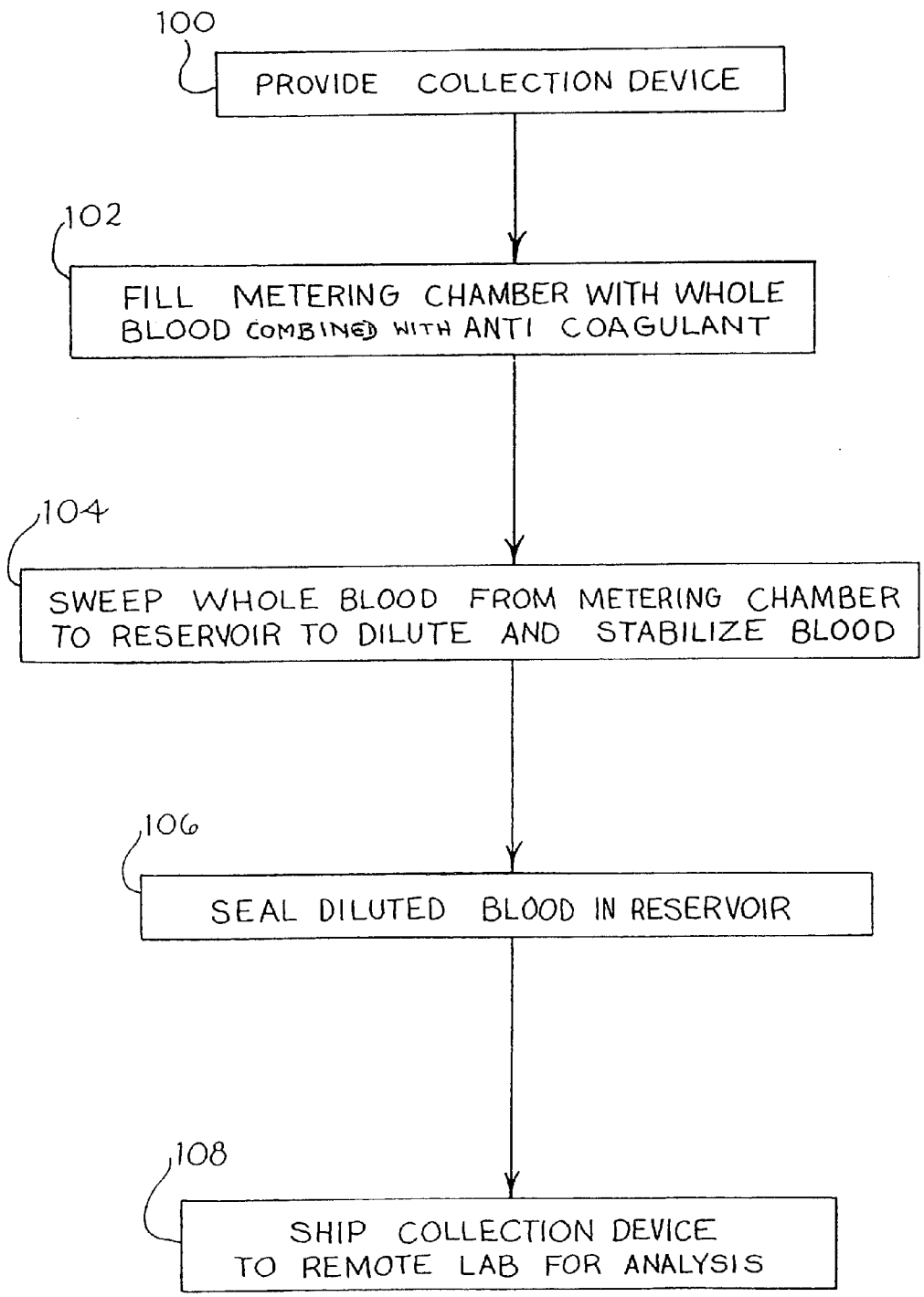
FIG. 24 is a flow chart of a method for collecting whole blood for remote analysis.

As shown in block 102 of FIG. 24, the metering chamber formed by the capillary channel 72 is then filled with whole blood mixed with anticoagulant. Blood obtained, for example, with a finger stick, flows through the fill port 32 into the capillary channel 72. In so doing, the blood passes through the anticoagulant pad 38 located directly under the fill port 32. Blood wets and passes through the pad 38, causing anticoagulant chemicals to leach from the pad 38 and mix with the blood. In this way, premature blood clotting is prevented and blood is maintained in a liquid state until it mixes with the reagents in the reservoir 74. Alternatively, anticoagulant can be delivered to the blood sample by a coating of anticoagulant on the surfaces of gasket or seal 16 and upper plate 12 that come into contact with the blood.

After the capillary channel 72 is filled, blood flows upwardly toward the view port 36 and into contact with the view port pad 40. After the pad 40 becomes saturated with blood, the view port 36 turns red, indicating to the user that the capillary channel 72 is full, and that the user can stop adding blood to the fill port 32. The view port 36 does not turn red until the capillary channel 72 is completely filled with blood. In this way, the capillary channel 72 operates as a metering chamber. User-to-user differences in blood drop volume are taken into consideration, because the user continues to add blood to the device until the view port 36 turns red. In this way a precise volume of blood is collected in the capillary channel 72, in spite of differences blood drop volume among users.

View port pad 40 can be composed of filter paper, such as Schleicher & Schuell 900 paper, a porous plastic material, and the like.

As shown at block 104 in FIG. 24, and in FIGS. 22 and 23, as handles 30, 70 and 50 are aligned with one another, blood is then swept from the capillary channel 72 to the reservoir 74 to dilute and stabilize the blood. FIG. 22 schematically shows selected elements of the device 10 in an intermediate position between the fill position and the closed position. Note that the handle 50 has been rotated counterclockwise (i.e., closer to handles 30, 70) in a view of FIG. 22 to sweep the blood from the capillary channel 72 into the reservoir 74 and to seal the fill port 32. The sweeping element 66 acts as a squeegee to sweep blood out of the capillary channel 72 and into the reservoir 74. The handles 30, 70 can be grasped by the user to facilitate counterclockwise movement of the handle 50.

As shown at block 106 of FIG. 24 and in FIG. 23, blood is then sealed in the reservoir 74. In this embodiment, the reservoir 74 initially contains a diluting liquid that optionally includes a blood stabilizing composition. The diluting liquid and the blood stabilizing composition can be inserted into the reservoir 74 by the device manufacturer via the access ports 78 before the plug 80 is applied. As shown at FIG. 23, once the handle 50 is moved to the closed position (i.e., substantially overlapping with handles 30, 70), the first portion 62 of the protruding element 60 substantially fills the capillary channel 72 and seals the reservoir 74 at both ends. The fill port 32 and the view port 36 are also closed by the gasket 16 in this position. In the closed position of FIG. 23, the handle 50 is aligned with the handles 30, 70, and the handle 50 is preferably held in the closed position by the latch described above and shown in FIG. 16. In this way the diluted blood is sealed in the reservoir for storage and shipment to a clinical laboratory for blood analyte analysis.

As shown in block 108 of FIG. 24, the blood filled collection device subsequently is shipped to a remote site for analysis. The device and the blood contained therein may be maintained at ambient temperature for storage and transport.

The remote site of block 108 can be any site at which blood analysis can be performed, such as a hospital, a clinic, a pharmacy, or a suitably equipped home. Once the collection device 10 reaches the remote site, the diluted, stabilized whole blood is then removed from the reservoir 74 via the access ports 78 after the plug 80 has been removed.

The diluting liquid or diluent in the reservoir increases the liquid volume of the sample that is available for analysis. This facilitates analysis. The volume of the reservoir is at least as great as the volume of the metering chamber, and can be at up to ten times as great as the volume of the metering chamber. Intermediate volumes of the reservoir can be about three to about nine times the volume of the metering chamber, so that corresponding volumes of diluting liquid can be used. In one preferred embodiment, the volume of the reservoir is about six times the volume of the metering chamber.

Simply by way of example, and without intending any limitation, the following preferred dimensions and materials have been found suitable for use in one preferred embodiment.

DIMENSIONS TABLE

| Element | Preferred Dimensions |
| --- | --- |
| metering chamber width | 0.075 inch |
| metering chamber depth | 0.075 inch |
| metering chamber volume | 50–150 µL |
| reservoir volume | 300–900 µL |
| diluting liquid volume | 200–700 µL |

MATERIALS TABLE

| Element | Preferred Material |
| --- | --- |
| plates 12, 14, 18 | polyethylene, polystyrene |
| gasket or seal 16 | styrene/ethylene/butylene polymer |
| anticoagulant pad 38 | polyethylene |
| view port pad 40 | polyethylene; filter paper |
| anticoagulant composition | EDTA or heparin |

The diluting liquid (stabilizer solution) will vary widely, depending on the application. Exemplary diluting liquid compositions are provided below.

1. EDTA, buffer, glucose, preservative, sodium chloride, stabilizers and water;
2. Citric acid, buffer, glucose, preservative, sodium chloride, stabilizers and water;
3. Formalin, ethanol, sodium chloride, stabilizers and water;
4. EDTA, sodium azide, ethanol, ethylene glycol, and water.

The preservatives of these examples may be any substance that inhibits bacterial or fungal growth, such as sodium azide, PROCLIN® (a product of Supelco, Bellefonte, Pa.) or any number of other chemical agents. The stabilizers of these examples can be any substance designed to stabilize the analytical component of interest, such as sucrose and detergents (both ionic and nonionic). The buffers of these examples can be any component designed to stabilize the pH of the diluting liquid. The preservative, buffer and stabilizer may or may not be included in the diluting liquid, depending on the intended use of the collected sample.

Of course, it should be understood that a wide range of changes and modifications can be made to the preferred embodiment described above. The gasket 16 operates as a seal, and in this embodiment the seal is formed in one piece. In an alternative embodiment, the seal can be formed from two or more sealing pasts.

The preferred embodiment described above utilizes a rotary motion to sweep blood from the metering chamber into the reservoir. In alternative embodiments a linear motion can be used. Also, in some alternative embodiments blood is swept from the metering chamber into the reservoir by pneumatic pressure rather than the squeegee action described above.

Additionally, the metering chamber may be larger than a capillary channel, and the reservoir may or may not contain a diluting liquid.

As used herein the term "position" is intended broadly to encompass a range of positions. For example, the intermediate position described above can correspond to any one of a range of positions.

The term "concentric" is intended broadly to encompass structure that extends over a full 360 degrees or all over only a fraction of 360 degrees.

The term "blood stabilizing composition" is intended broadly to encompass any composition for stabilizing one or more selected components of whole blood.

In addition to the anticoagulant present in the anticoagulant pad 38, the anticoagulant can be coated onto portions of the device 10 that come into contact with blood during use. For example, gasket 16 and upper plate 12, or a portion thereof, can be coated with an anticoagulant.

In one preferred embodiment, gasket 16 is treated with an anticoagulant solution, and dried to form a coating of anticoagulant on gasket 16. Treatment of the gasket includes spraying a solution of anticoagulant onto the gasket or soaking the gasket in an anticoagulant solution, and subsequent drying of the sprayed or soaked gasket to deposit an anticoagulant coating thereon.

In another preferred embodiment, upper plate 12 is treated with an anticoagulant solution and dried to form a coating of anticoagulant on plate 12. Treatment of the upper plate 12 includes spraying a solution of anticoagulant onto the entire upper surface of the plate, spraying an anticoagulant solution onto the portion of the upper plate 12 defining the fill port 32 and the funnel portion 34, or soaking the upper plate 12 in an anticoagulant solution, and subsequent drying of the sprayed or plate gasket to deposit an anticoagulant coating thereon.

In yet another preferred embodiment, both the upper plate 12 and the gasket 16 are treated with anticoagulant as described above, such than both the gasket 16 and at least a portion of the upper plate 12 is coated with anticoagulant. Preferably, at least the funnel 34 and the portion of upper plate 12 defining fill port 32 are coated with anticoagulant.

Alternatively, in the embodiments in which the gasket 16 and/or the upper plate 12 are coated with anticoagulant, the anticoagulant pad 38 can be omitted.

Anticoagulants suitable for use in coating the gasket 16 and upper plate 12 include any non-crystallizing anticoagulant. Preferably the anticoagulant is heparin, citric acid, EDTA or noncrystalline salts thereof, and non-crystalline combinations thereof. Crystallization inhibiting agents, such as non-volatile solvents, e.g. propylene glycol, polyethylene glycols, and like materials, can be added to the treatment solution containing anticoagulant to prevent crystallization upon drying. A particularly preferred anticoagulant for coating portions of the device of the present invention is the sodium salt of heparin.

Preferably the anticoagulant solution utilized to treat the upper plate 12 and gasket 16 contains a wetting agent such as a nonionic surfactant. Suitable nonionic surfactants are disclosed in 2001 *McCutcheon's* Directories, Volume 1: Emulsifiers & Detergents published by McCutcheon's Division, The Manufacturing Confectioner Publishing Co. Glen Rock, N.J. (2001), the relevant disclosures of which are incorporated herein by reference. Preferred nonionic surfactants include polyoxyethylenesorbitan monooleates, such as TWEEN® 80, polyoxyethylenesorbitan monolaurates such as TWEEN® 20 polyoxyethylenesorbitan monopalmitates such as TWEEN® 40, polyoxyethylenesorbitan monostearates such as TWEEN® 60 and 61, polyoxyethylenesorbitan tristearates such as TWEEN® 65, and polyoxyethylenesorbitan trioleates such as TWEEN® 85, all of which are commercially available from ICI Americas, Bridgewater, N.J. Most preferably the wetting agent is a polyoxyethylenesorbitan monooleate, such as TWEEN® 80.

Preferably, the wetting agent is included in the anticoagulant treatment solution in a concentration in the range of about 0.01 to about 5 percent by weight, more preferably in the range of about 0.1 to about 3 percent by weight.

Preferably, the anticoagulant coating contains a sufficient quantity of anticoagulant in the coated regions of the device that come into contact with blood to transfer about 1.25 to about 12.5 USP units (U) of anticoagulant to a 150 µL blood sample deposited in the device 10. More preferably, about 3 to about 4 U of anticoagulant per 150 µL of sample are introduced into the whole blood sample received in the device embodying the present invention.

A preferred formulation and procedure for treating the device of the present invention to deposit an anticoagulant coating thereon is provided below by way of example.

EXAMPLE 1

Coating Solution A. A treatment solution was prepared by combining about 800 mg of sodium heparin (Sodium salt from Porcine Intestinal Mucosa, Activity: 173 USP units per mg), about 10 g of TWEEN® 80 (equivalent to 0.5 weight percent of active surfactant) in about 19.9 Kg of water and stirring the resulting mixture for a time sufficient to form a homogeneous solution (about 10 minutes).

EXAMPLE 2

Coating Procedure. Seals 16, fabricated from KRATON® thermoplastic rubber (Kraton Polymers, Houston, Tex.), and upper plates 12, fabricated from polystyrene, were soaked in the Coating Solution A for about 15 minutes, with gentle agitation. The seals and plates were removed from the coating solution and dried for about 24 hours at a temperature in the range of about 24 to about 32° C.

EXAMPLE 3

Evaluation of Anticoagulant Delivery to Blood Samples. The coated seals and upper plates from Example 2 were assembled into complete blood collection devices of the invention, without the anticoagulant pad 38. Each device had a blood metering chamber (capillary channel 72) with a volume of about 80 µL, and a reservoir 74 having a volume of about 350 µL containing about 200 µL of a stabilizing solution.

The stabilizing solution contained about 13 parts by weight of disodium EDTA, about 0.22 parts by weight of sodium azide, about 76 parts by weight of ethanol, and about 486 parts by weight of ethylene glycol, dissolved in about 437 parts by weight of deionized water.

Sufficient blood (obtained from a finger nick) to produce a red color in the view port 36 was added to each of the assembled devices with handle 50 (and the seal/gasket 16) in the fill position. Handle 50 was rotated counterclockwise to align with handle 30, 70 as described above, to sweep the blood into the reservoir 74, sealing the reservoir and diluting the blood therein.

The diluted blood was removed from each device by removal of plug 80 from the reservoir 74, and the heparin activity of the diluted blood was determined by a USP bioassay. On average, a heparin activity of about 3.46 USP units per blood sample was obtained for the diluted blood samples. A heparin activity in the range of about 1.25 to about 12.5 USP units per sample is considered acceptable for typical blood assays such as assays for TSH, PSA, and CBC. Each device was also disassembled and the seal 16 and capillary channel 72 were inspected for blood clots. No clots were observed.

Numerous variations and modifications of the embodiments described above can be effected without departing from the spirit and scope of the novel features of the invention. No limitations with respect to the specific embodiments illustrated herein are intended or should be inferred. The above disclosure is intended to cover by the appended claims all such modifications as fall within the scope of the claims.

We claim:

1. A whole blood sample collection device comprising:
   a reservoir;
   a metering chamber that empties into the reservoir;
   a fill port that empties into the metering chamber; and
   a seal comprising a sweeping element movable between a fill position, in which the seal isolates the reservoir from the metering chamber while defining a liquid flow passageway between the fill port and the metering chamber; an intermediate position in which the seal isolates the metering chamber from the fill port and from the reservoir; and a closed position, in which the seal isolates the fill port from the metering chamber but provides fluid flow communication between the reservoir and the metering chamber;
   said reservoir, metering chamber, fill port and seal forming a portable, handheld unit and said fill port, metering chamber and seal together defining a sample passageway; and at least a portion of the sample passageway being coated with an anticoagulant.

2. The device of claim 1 wherein the seal comprises a first side that faces the fill port and a second side that faces the reservoir and the metering chamber.

3. The device of claim 1 wherein the metering chamber comprises a capillary channel.

4. The device of claim 3 further comprising a view port in fluid communication with the capillary channel, said view port being spaced from the fill port along the channel.

5. The device of claim 1 wherein the a sweeping element is sized to fit within the metering chamber and the sweeping element is movable along the metering chamber to sweep blood received in the metering chamber to the reservoir.

6. The device of claim 5 wherein the fill port is defined by a portion of an upper plate; the metering chamber and the reservoir are defined by a lower plate; and the seal is movably disposed between the upper and lower plates.

7. The device of claim 6 wherein the portion of the upper plate defining the fill port is coated with an anticoagulant.

8. The device of claim 6 wherein the seal and the upper plate are coated with an anticoagulant.

9. The device of claim 6 wherein the seal is mounted for rotation relative to the upper and lower plates about an axis substantially normal to said plates, and wherein the sweeping element and the metering chamber are concentric with the axis.

10. The device of claim 9 wherein the seal extends over an arc of about 270 degrees and the metering chamber extends over an arc of about 90 degrees.

11. The device of claim 5 wherein the metering chamber and the sweeping element are arcuate in shape.

12. The device of claim 1 wherein the reservoir includes a diluting liquid.

13. The device of claim 12 wherein the diluting liquid comprises a blood stabilizing composition.

14. The device of claim 12 wherein the metering chamber defines a first volume, and wherein the diluting liquid has a volume at least as great as nine times the first volume.

15. The device of claim 1 wherein the metering chamber defines a first volume, and wherein the reservoir defines a volume greater than the first volume.

16. The device of claim 15 wherein the metering chamber defines a first volume, and wherein the reservoir defines a volume at least as great as three times the first volume.

17. The device of claim 15 wherein the metering chamber defines a first volume, and wherein the reservoir defines a volume at least as great as six times the first volume.

18. The device of claim 1 further comprising a porous pad disposed between the fill port and the metering chamber, wherein the pad contains an anticoagulant.

19. The device of claim 1 wherein the reservoir and the metering chamber are fixedly positioned with respect to one another.

20. The device of claim 1 wherein the reservoir and the metering chamber remain in a fixed spatial position relative to one another as the seal is moved from the fill position to the closed position.

21. The device of claim 1 further comprising a snap latch operative to retain the seal in the closed position.

22. The device of claim 1 wherein the fill port, the metering chamber and the reservoir are each coated with an anticoagulant.

23. The device of claim 1 wherein the anticoagulant is selected from the group consisting of heparin, EDTA, citric acid, and noncrystalline salts from said group.

24. A whole blood sample collection device comprising:
   a reservoir;
   a metering chamber that empties into the reservoir;
   a fill port that empties into the metering chamber; and
   a seal movable between a fill position, in which the seal isolates the reservoir from the meeting chamber while defining a fluid flow passageway between the fill port and the metering chamber; and a closed position, in which the seal isolates the fill port from the metering chamber and provides fluid flow communication with the reservoir and the metering chamber;
   wherein the seal comprises a first side that faces the fill port and a second side that faces the reservoir and the metering chamber; and the interior of at least one of the fill port and metering chamber, is coated with an anticoagulant.

25. The device of claim 24 wherein the anticoagulant is selected from the group consisting of heparin, EDTA, citric acid, and noncrystalline salts from said group.

26. A whole blood sample collection device comprising:
   a reservoir;
   a metering chamber that empties into the reservoir;

a fill port that empties into the metering chamber; and a seal movable between a fill position, in which the seal isolates the reservoir from the metering chamber while defining a fluid flow passageway between the fill port and the metering chamber; and a closed position, in which the seal isolates the fill port from the metering chamber and defines a fluid flow passageway between the reservoir and the metering chamber;

wherein the seal comprises a sweeping element sized to fit within the metering chamber, wherein the sweeping element is movable along the metering chamber to sweep fluid from the metering chamber to the reservoir as the seal moves from the fill position to the closed position; and at least one of the fill port, metering chamber, and the sweeping element is coated with an anticoagulant.

27. The device of claim 26 wherein the anticoagulant is selected from the group consisting of heparin, EDTA, citric acid, and noncrystalline salts from said group.

28. A whole blood sample collection device comprising:

a reservoir;

a metering chamber that empties into the reservoir;

a fill port that empties into the metering chamber; and a seal movable between a fill position, in which the seal isolates the reservoir from the metering chamber while defining a fluid flow passageway between the fill port and the metering chamber; and a closed position, in which the seal isolates the fill port from the metering chamber and defines a fluid flow passageway between the reservoir and the metering chamber;

wherein the fill port, metering chamber, and the seal define a sample passageway provided with an anticoagulant.

29. The device of claim 28 wherein the anticoagulant is selected from the group consisting of heparin, EDTA, citric acid, and noncrystalline salts from said group.

30. A whole blood sample collection device comprising:

a reservoir;

a metering chamber that empties into the reservoir;

a fill port that empties into the metering chamber; and a seal movable between a fill position, in which the seal isolates the reservoir from the metering chamber while defining a fluid flow passageway between the fill port and the metering chamber; and a closed position, in which the seal isolates the fill port from the metering chamber and defines a fluid flow passageway between the reservoir and the metering chamber;

wherein the device defines a capillary channel and a view port in fluid communication with the capillary channel, said view port being spaced from the fill port along the channel;

wherein the seal closes the fill port and the view port when in the closed position; and wherein at least one of the fill port, metering chamber, and the seal is coated with an anticoagulant.

31. The device of claim 30 wherein the anticoagulant is selected from the group consisting of heparin, EDTA, citric acid, and noncrystalline salts from said group.

* * * * *